US00PP24838P2

(12) United States Plant Patent
de Vos

(10) Patent No.: US PP24,838 P2
(45) Date of Patent: Sep. 2, 2014

(54) *ABELIA* 'WEVO2'

(50) Latin Name: *Abelia×grandiflora*
Varietal Denomination: Wevo2

(71) Applicant: Lendert de Vos, Reeuwijk (NL)

(72) Inventor: Lendert de Vos, Reeuwijk (NL)

( * ) Notice: Subject to any disclaimer, the term of this patent is extended or adjusted under 35 U.S.C. 154(b) by 147 days.

(21) Appl. No.: 13/573,876

(22) Filed: Oct. 11, 2012

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Wendy C Haas
(74) *Attorney, Agent, or Firm* — Penny J. Aguirre

(57) ABSTRACT

A new cultivar of *Abelia×grandiflora* named 'Wevo2' that is characterized by its foliage that is shiny and medium green in color and variegated with a thin white margin; the variegation is retained from spring until winter, its white flowers, and its dwarf and upright spreading plant habit.

2 Drawing Sheets

Botanical classification: *Abelia×grandiflora*.
Varietal denomination: 'Wevo2'.

BACKGROUND OF THE INVENTION

The present invention relates to a new and distinct cultivar of *Abelia×grandiflora* and will be referred to hereafter by its cultivar name, 'Wevo2'. 'Wevo2' represents a new *Abelia*, a semi-evergreen shrub grown for landscape use.

The Inventor discovered the new cultivar in summer of 2007 as a naturally occurring branch mutation of *Abelia×grandiflora* 'Abelops' (U.S. Pat. No. 20,961) in a container at his nursery in Reeuwijk, The Netherlands.

Asexual reproduction of the new cultivar was first accomplished by stem cutting by the inventor in Reeuwijk, The Netherlands in 2007. It has been determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Wevo2' from all other varieties of *Abelia* known to the inventor.

1. 'Wevo2' exhibits foliage that is shiny and medium green in color and variegated with a thin white margin; the variegation is retained from spring until winter.
2. 'Wevo2' exhibits white flowers.
3. 'Wevo2' exhibits a dwarf and upright spreading plant habit; reaching about 1 m in height when mature.

'Abelops', the parent plant of 'Wevo2', differs from 'Wevo2' in having variegated foliage in which the white margin is wider, in having foliage that turns reddish in autumn, and in having flowers that are pinkish white in color. 'Wevo2' can also be most compared to the cultivar 'Kaleidoscope' (U.S. Plant Pat. No. 16,988), 'Conti' (not patented) and 'Sunrise' (not patented). 'Kaleidoscope' differs from 'Wevo2' in having variegated foliage with green centers and wide yellow margins early in season with the leaves flushed with orange and red in autumn. 'Conti' differs from 'Wevo2' in having foliage that is variegated with broader white margins that are flushed with pink on new growth, and in having flowers that are pinkish white in color. 'Sunrise' differs from 'Wevo2' in having variegated foliage with wider margins that are golden yellow in color and turn to creamy white as the leaves mature.

BRIEF DESCRIPTION OF THE PHOTOGRAPHS

The plants and plant parts in the photographs depict a two-year old plant of 'Wevo2' as grown in an unheated greenhouse in a 15-cm container in Reeuwijk, The Netherlands.

Figure 1:
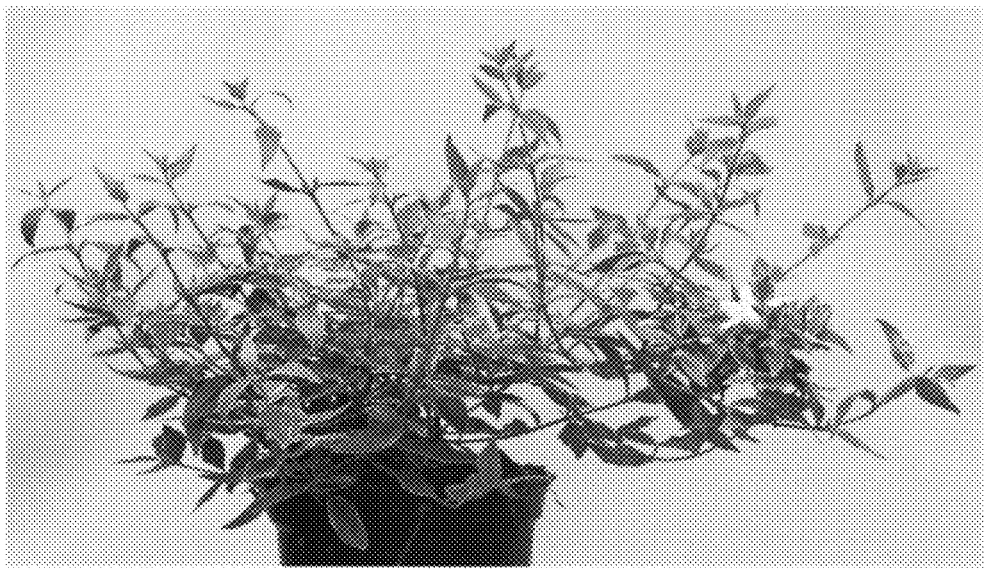

The photograph in FIG. 1 provides a side view of 'Wevo2'.

Figure 2:
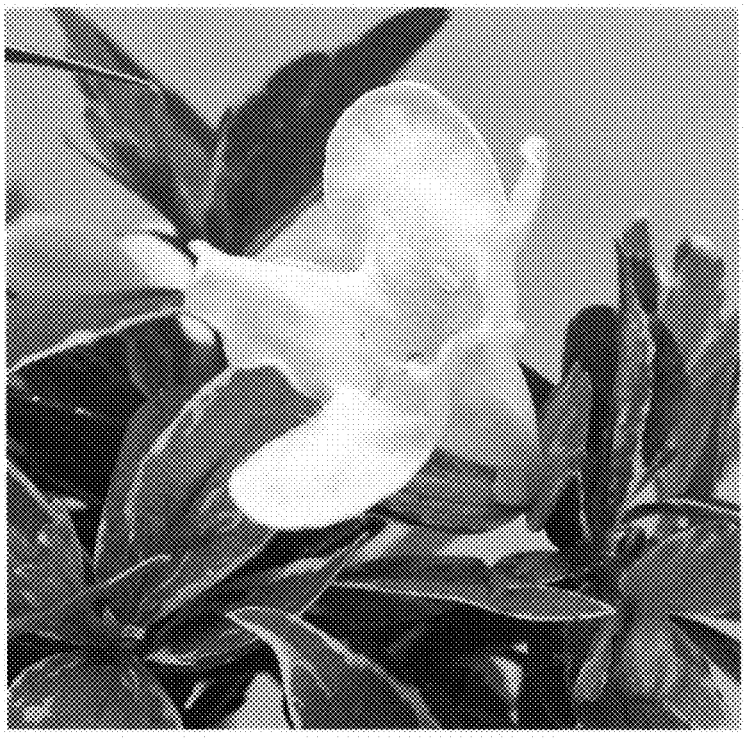

The photograph in FIG. 2 provides a close-up view of a flower of 'Wevo2'.

Figure 3:
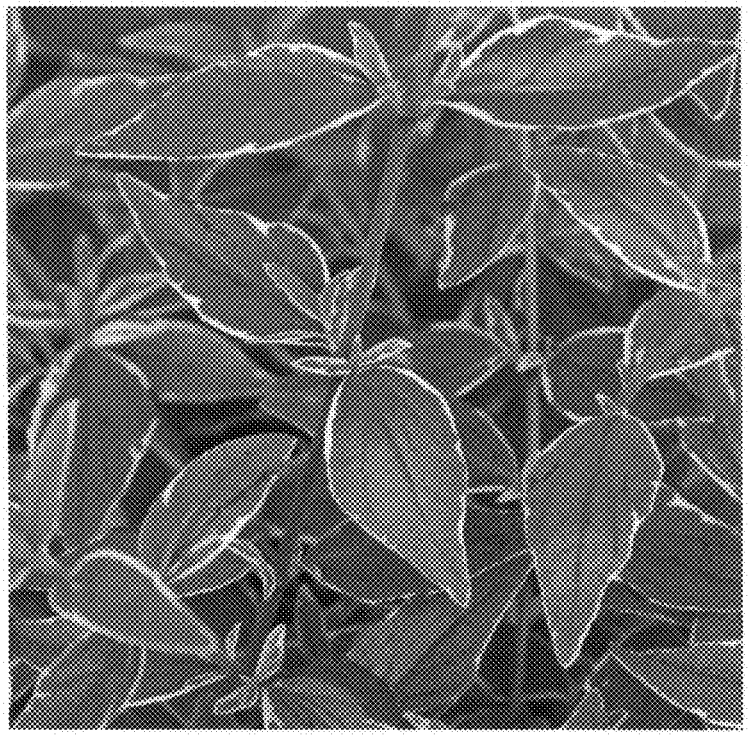

The photograph in FIG. 3 provides a close-up the foliage of 'Wevo2'. The colors in the photographs are as close as possible with the photographic and printing technology utilized and the color values cited in the detailed botanical description accurately describe the colors of the new *Abelia*.

DETAILED BOTANICAL DESCRIPTION

The following is a detailed description of two year-old plants of the new cultivar as grown in an unheated greenhouse in 15-cm containers in Reeuwijk, The Netherlands with average day temperatures ranging from 10° C. to 24° C. and average night temperatures ranging from 2° C. to 14° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Mid July to October in The Netherlands.

*Plant type.*—Semi-evergreen shrub.

*Plant habit.*—Dwarf, spreading and broadly upright.

*Height and spread*.—Average of 22 cm in height and 43 cm in spread in as grown in a 15-cm container, reaching about 1 m in height and 1.5 m in width in the landscape.

*Cold hardiness*.—At least to U.S.D.A. Zone 7a.

*Diseases and pests*.—No susceptibility or resistance to pests and diseases has been.

*Propagation*.—Stem cuttings.

*Growth rate*.—Moderate.

Stem description:

*Stem color*.—Young and mature stems; between 176B and 177A.

*Stem size*.—Average of 14.2 cm in length and 2 mm in diameter.

*Stem quantity*.—Average of 35.

*Stem shape*.—Rounded.

*Stem surface*.—Moderately glossy with densely pubescent very short glandular hairs, average of 0.1 mm in length.

*Stem aspect*.—Very strong.

*Branching habit*.—Free branching.

Foliage description:

*Leaf division*.—Single.

*Leaf attachment*.—Petiolate.

*Leaf arrangement*.—Opposite.

*Leaf number*.—Average of 10.

*Leaf shape*.—Ovate to irregular ovate.

*Leaf apex*.—Acute.

*Leaf surface*.—Glabrous and glossy on upper surface, glabrous and dull on lower surface.

*Leaf base*.—Short attenuate.

*Leaf venation*.—Pinnate, color upper surface between N137C and 147A, color lower surface 191B to 191C.

*Leaf margin*.—Entire.

*Leaf color*.—Immature upper surface; 143A with irregularly narrow margins 154C, immature lower surface; 138B with irregular narrow margins 154C to 154D, mature upper surface; becoming N137C and 147A with irregular narrow margins 155A, mature lower surface; 191A with irregular narrow margins 155A to 155B.

*Internode*.—Average of 2.8 cm in length.

*Leaf size*.—Average of 3.7 cm in length and 1.8 cm in width.

*Petioles*.—Average of 1 mm in diameter and 3 mm in length, both surfaces 146C in color.

Flower description:

*Inflorescence type*.—Numerous single flowers arranged on terminal panicles.

*Inflorescence aspect*.—All directions.

*Inflorescence size*.—Average of 7.2 cm in height and 6.7 cm in width.

*Flower fragrance*.—Faint, sweet.

*Flower quantity*.—Average of 27 per inflorescence.

*Flower lastingness*.—Average of 5 days.

*Flower buds*.—Obovate in shape, curved downward, average of 8 mm in diameter and 2.1 cm in length, color; N155B, top becoming NN155A to NN155B, base 157D.

*Flower aspect*.—All directions.

*Flower shape*.—Campanulate with base fused.

*Flower size*.—About 3.1 cm in depth and 2.2 cm in diameter.

*Petals*.—Average of 5, oblong in shape, margin is entire, apex is obtuse, upper surface is smooth and covered with soft hairs 1 mm in length and NN155C to NN155D in color, lower surface smooth and slightly glossy, color: upper surface when opening; NN155C to NN155D, lower surface when opening; NN155C to NN155D with the top becoming slightly darker; NN155A, upper surface when fully opened; NN155C to NN155D, lower surface when fully opened; NN155C to NN155D with the top becoming slightly darker; NN155A average of 2.4 cm in length and 8 mm in width, 66% of the lower petals fused.

*Calyx*.—Rotate, average of 9 mm in length and 1.3 cm in diameter.

*Sepals*.—5, occasionally 2 or 3 sepals are fused, narrow elliptic in shape, margin is entire, apex is obtuse, base is cuneate, surface is smooth and dull, color: immature upper surface; becoming 138B or 141C and turning into 146A to 146B at the top with irregular margins 155A to 155B, immature lower surface; 138B and turning into 146A to 146B at the top with irregular margins 155A to 155B, mature upper and lower surfaces; 138B and turning into 146A to 146B at the top with irregular margins 155A to 155B, about 3 mm in width and 10 mm in length.

*Peduncles*.—Average of 5.8 cm in length and 1.5 mm in width, strong, color: upper surface; 177A to 177B, lower surface; 147B to 148B, glabrous surface, average angle of 0° (straight on top of lateral branch), secondary peduncles in an average angle of 45°.

*Pedicels*.—About 1 mm in length and 0.5 mm in width, strong, upper and lower surface 143B in color, glabrous surface, average angle: 0° (straight on top of peduncle), secondary pedicels in an average angle of 45°.

Reproductive organs:

*Gynoecium*.—1 pistil, club-shaped, about 1.8 mm in length, stigma N155A in color, style is about 1.7 mm in length and 157D in color, ovary is 143B in color.

*Androcoecium*.—About 4 stamens, anthers are oblong in shape, basifixed, about 2 mm in length and 156A in color, filaments are about 1.6 cm in length and NN155C to NN155D in color, pollen is low in quantity and 161B to 161C in color.

*Fruit and seed*.—No fruit or seed have been observed.

It is claimed:

1. A new and distinct cultivar of *Abelia* plant named 'Wevo2' as herein illustrated and described.

* * * * *